US006573413B2

(12) United States Patent
Chernyavsky et al.

(10) Patent No.: US 6,573,413 B2
(45) Date of Patent: Jun. 3, 2003

(54) PROCESS FOR ACTIVATING CATALYST FOR THE HYDROXYLATION OF AROMATICS

(75) Inventors: Valery S. Chernyavsky, Novosibirsk (RU); Alexander Sergeevich Kharitonov, Novosibirsk (RU); Gennady I. Panov, Novosibirsk (RU); Konstantin A. Dubkov, Novosibirsk (RU)

(73) Assignee: Solutia Inc., St. Louis, MO (US)

( * ) Notice: Subject to any disclaimer, the term of this patent is extended or adjusted under 35 U.S.C. 154(b) by 152 days.

(21) Appl. No.: 09/837,548

(22) Filed: Apr. 18, 2001

(65) Prior Publication Data

US 2002/0026085 A1 Feb. 28, 2002

Related U.S. Application Data

(60) Provisional application No. 60/198,361, filed on Apr. 19, 2000.

(51) Int. Cl.[7] .............................................. C07C 37/00
(52) U.S. Cl. ........................ 568/800; 502/34; 502/53; 502/54; 502/55; 568/771
(58) Field of Search ................ 568/800, 771; 502/34, 53, 54, 55

(56) References Cited

U.S. PATENT DOCUMENTS

| 4,150,064 A | 4/1979 | Miklas | 260/680 E |
|---|---|---|---|
| 4,224,190 A | 9/1980 | Villadsen et al. | 252/463 |
| 4,326,994 A | 4/1982 | Haag et al. | 252/455 Z |
| 4,418,028 A | 11/1983 | Schucker et al. | 502/340 |
| 4,425,260 A | 1/1984 | Ebner | 502/255 |
| 4,443,554 A | 4/1984 | Dessau | 502/71 |
| 4,452,693 A | 6/1984 | Schucker et al. | 208/121 |
| 4,497,903 A | 2/1985 | Kibby et al. | 502/85 |
| 4,547,482 A | 10/1985 | Osugi et al. | 502/208 |
| 4,670,414 A | 6/1987 | Kobykinski et al. | 502/174 |
| 4,748,140 A | 5/1988 | Blum et al. | 502/209 |
| 4,784,747 A | 11/1988 | Shihabi | 208/111 |
| 4,826,800 A | 5/1989 | McAteer | 502/303 |
| 4,829,039 A | 5/1989 | White et al. | 502/152 |
| 4,911,904 A | 3/1990 | Delzer et al. | 423/437 |
| 4,943,545 A | 7/1990 | Chang et al. | 502/56 |
| 5,308,822 A | 5/1994 | Iezzi et al. | 502/243 |
| 5,414,182 A | 5/1995 | Iezzi et al. | 585/661 |
| 5,444,132 A | 8/1995 | Witt et al. | 526/106 |
| 5,672,777 A | 9/1997 | Kharitonov et al. | 568/800 |
| 5,756,420 A | 5/1998 | Wittenbrink et al. | 502/313 |
| 5,874,647 A | 2/1999 | McGhee et al. | 568/800 |
| 5,892,132 A | 4/1999 | Rooks et al. | 568/771 |

FOREIGN PATENT DOCUMENTS

DE   196 34 406 A1   3/1998   ............... 255/53

*Primary Examiner*—Michael L. Shippen

(57) ABSTRACT

A method for catalytic production of hydroxylated aromatics by exposing zeolite catalyst to a reducing atmosphere to activate said catalyst, and reacting an aromatic with nitrous oxide in the presence of said activated catalyst.

24 Claims, No Drawings

PROCESS FOR ACTIVATING CATALYST FOR THE HYDROXYLATION OF AROMATICS

This case claims the benefit of Provisional Application Serial No. 60/198,361 filed Apr. 19, 2000.

FIELD OF THE INVENTION

The present invention relates to the activation of catalysts for hydroxylation of aromatics. The present invention also relates to restoring activity of deactivated hydroxylation catalysts and to preventing the loss of activity in such catalyst.

BACKGROUND OF THE INVENTION

Introduction of a hydroxyl group onto an aromatic ring is one of the most difficult problems of organic synthesis. The simplest reaction of this type, benzene oxidation to phenol, is conducted presently by the so-called cumene process involving three stages. Numerous efforts to perform a direct benzene oxidation to phenol with molecular oxygen have not been successful. Interaction with oxygen results in a cleavage of the benzene ring and a low phenol selectivity.

The production of hydroxylated aromatics by partial oxidation of aromatics using nitrous oxide over zeolites has been demonstrated. See U.S. Pat. Nos. 5,055,623; 5,001,280; 5,110,995; and 5,756,861, the subject matter of which is incorporated herein by reference in its entirety. The most commonly utilized hydroxylated aromatic is phenol, which is used primarily in production of phenolic resins, caprolacturn, nitrophenols, chlorophenols, etc.

Various problems have been encountered in efforts to commercialize a viable aromatic hydroxylation process. One such problem lies in the activation and deactivation of catalysts utilized in such processes, in particular the activation and deactivation of zeolite catalysts. Zeolite catalysts inherently possess several drawbacks, namely low activity and gradual deactivation, leading to the eventual need to replace the catalyst.

While there are many explanations and theories as why zeolite catalysts are problematic with regard to activation and deactivation for aromatic hydroxylation reactions with accompanying solutions to such problems, no solution has been achieved that provides a noticeable improvement to existing processes. Various processes have been used to activate zeolite catalysts for aromatic hydroxylation reactions. For example, Zholobenzlo reported in *Mendeleev Commun.* (1993) No. 1, pg. 28–29, a method for phenol production using zeolite catalyst that had been activated by high temperature calcination in air (e.g., 350–1000° C.). In U.S. Pat. Nos. 5,672,777; 4,002,578; and German Patent Application No. DE 196 34 406 A1, the subject matter of which is incorporated herein in its entirety, discloses the activation zeolite catalyst for use in aromatic hydroxylation reactions by hydrothermal treatment (e.g., 350–950° C.) of the catalyst using steam in an inert gas carrier. However, the above-mentioned activation processes do not significantly increase the activation of the catalysts.

As described in U.S. Pat. Nos. 4,784,747 and 4,443,554, the entire subject matter of which is incorporated herein, the use of an inert gas in the steaming activation of zeolite catalysts (utilized for a variety of reactions) is essential. As prescribed in these patents, reducing gases are to be avoided due to the negative impact on such gases to the acidity of the catalyst, which is believed to provide catalyst activity.

Reductive treatment has been utilized for the activation of supported metal catalysts used in the reactions of ammonia synthesis or hydrogenation of various organic compounds. Sometimes such a reductive treatment is employed for zeolite catalysts to increase their activity prior to reactions proceeding in a reducing atmosphere, without the presence of an oxidant. For example, U.S. Pat. No. 4,002,578, the entire subject matter of which is incorporated herein by reference, discloses an activation method for zeolites, containing metals of the VIII group, by treatment of such zeolites in hydrogen at 250–650° C. Such treatment increases the catalytic activity of zeolites in hydrogenation reactions. In U.S. Pat. No. 4,539,305, the entire subject matter of which is incorporated herein by reference, a similar reductive treatment of zeolite catalysts is carried out to increase such catalysts activity in reforming processes. In U.S. Pat. No. 4,326,994, the entire subject matter of which is incorporated herein by reference, a zeolite activation method is described in which the zeolite is treated with water vapor and in the presence of ammonia as well. This improves the zeolite catalytic properties with regard to cracking, hydrocracking, alkylation, dealkylation, isomerization and aromatization of hydrocarbons.

However, it is not known to utilize a reductive treatment with zeolite catalysts when such catalysts are employed in oxidation reactions, since such treatment would be expected by the artisan to degrade catalytic activity for such reactions. In particular, heterogeneous catalytic oxidation reactions proceed generally in the range of rather high temperatures (above 300° C.). At such temperatures, any contact of the reduced catalyst with an oxidant would expectedly cause catalyst oxidation, thus rendering the catalyst in a state equivalent to the catalyst prior to the reductive treatment. In addition, any catalyst treatments, such as the reductive treatment followed by oxidation, would be expected to cause thermal/physical damages to the catalyst. Accordingly, for application in oxidation reactions, reductive pretreatment would be expected by the artisan to provide negligible catalyst activity improvement, and moreover, may likely damage the catalyst.

Other catalyst activation processes include the use of steam and reducing gases. See U.S. Pat. Nos. 4,150,064; 4,748,140; 5,308,822; 4,826,800; 4,547,482; 4,452,693; and 4,911,904, the entire subject matter of which is incorporated herein by reference. However, such processes treat non-zeolite catalysts that are comprised of materials and structures quite diverse from zeolite catalysts, and are accordingly, utilized for catalyzing reactions significantly different from hydroxylation reactions. Thus, activation of zeolite catalysts utilized for oxidation reactions has heretofore not included use of steam and reducing gases.

SUMMARY OF THE INVENTION

The present invention provides for a method for catalytic production of hydroxylated aromatic compounds by exposing a zeolite catalyst to an atmosphere of reducing gas to activate the catalyst, and reacting an aromatic compound with nitrous oxide in the presence of the activated catalyst. Also, the present invention concerns a method for restoring activity of a deactivated zeolite catalyst by exposing the zeolite catalyst to an atmosphere of reducing gas. Moreover, the present invention relates to a method for reducing activity loss of a zeolite catalyst during production of hydroxylated aromatics by reacting an aromatic compound with nitrous oxide in the presence of the zeolite catalyst, and exposing the catalyst during the reaction to an atmosphere of reducing gas.

DESCRIPTION OF ILLUSTRATIVE EMBODIMENTS

In accordance with the present invention, a zeolite catalyst is activated by exposing said catalyst to reducing atmosphere to thereby render the catalyst suitable for use in hydroxylation of various compounds, including aromatics and substituted aromatics. Such activated catalyst may be utilized in commercial hydroxylation of aromatics, such as in one-step hydroxylation of benzene to phenol as set forth in U.S. Pat. Nos. 4,982,013; 5,001,280; 5,055,623; 5,110,995; 5,672,777; 5,756,861; and 5,808,167, the entire subject matter of which is incorporated herein by reference.

In one embodiment of the present invention, a zeolite catalyst is activated by exposing the catalyst to a reducing gas and water vapor. The zeolite catalyst may include zeolites of various chemical compositions having a pentasyl or beta type structure, such as those set forth in U.S. Pat. Nos. 4,982,013; 5,001,280; 5,055,623; 5,110,995; 5,672,777; 5,756,861; and 5,808,167, the entire subject matter of which is incorporated herein by reference. For example, the zeolite catalyst may include ZSM-5 and ZSM-11 zeolite catalysts containing a catalytically effective amount (e.g., up to 2 wt %) of transition metal, such as one or more elements of Group 2–6, with iron being a preferred transition metal. More preferably, the catalysts comprise acidified ZSM-5 and ZSM-11 zeolites containing a catalytically effective amount of iron.

The catalyst may be prepared according to conventional methods, as described in the U.S. Pat. Nos. 4,982,013; 5,001,280; 5,055,623; 5,110,995; 5,672,777; 5,756,861; and 5,808,167. For example, a gel comprising organic and zeolitic material is formed followed by hydrothermal treatment to remove the organic material and form the zeolitic microporous structure. Transition metal may be introduced at the stage of zeolite synthesis as well as by various postsynthesis treatments, e.g. by impregnation or chemical diffusion from the gas phase. The catalyst may be used both formed (e.g., in bound form) and unformed (e.g., in powder form). Upon forming, Al, Si, Ti, etc. oxides or mixtures of them may be used as a binder, i.e., the oxides conventionally used for this purpose. Following conventional pretreatment processes, the catalyst is then exposed to an atmosphere of a reducing gas.

The reductive treatment may be conducted before and/or after the catalyst is formed with the binder. The reducing gas may include hydrogen, ammonia, carbon monoxide, hydrogen monoxide, methane, ethane, benzene, methanol, ethanol and mixtures thereof, or any gas that may provide a reducing atmosphere for the catalyst. Preferably, the reducing gas is carbon monoxide. The amount of reducing gas in the reducing atmosphere may range from about 0.01 to about 100 vol. %, preferably from about 1 to about 50 vol. %, and more preferably from about 2 to about 10 vol. %. Preferably, the amount of reducing gas in the reducing atmosphere does not exceed the lower limit of the atmosphere's flashpoint in order to avoid the formation of an explosive mixture in the event of unexpected depressurization of the reactor. The reducing atmosphere may also include water vapor. The amount of water vapor in the reducing atmosphere may range from about 1 to about 99.9 vol. %, preferably about 10 to about 90 vol. %, and more preferably about 30 to about 60 vol. %. Preferably, the water vapor is in the form of steam. If desirable, an inert gas may be utilized in an amount of up to about 99.9 vol. %. Preferably, the reducing atmosphere comprises from about 1 to about 50 vol. % of reducing gas, and from about 20 to about 80 vol. % of water vapor, with any remainder being inert gas. More preferably, the reducing atmosphere comprises from about 2 to about 10 vol. % of reducing gas, and from about 30 to about 60 vol. % of water vapor, with any remainder being inert gas.

Suitable temperatures for activation of the catalyst in the reducing atmosphere are about 300 to about 1000° C., preferably about 800 to about 900° C., and more preferably about 500 to about 700° C. Suitable time periods for exposure of the catalyst to the reducing atmosphere vary depending on the type of reductant, the temperature, and the catalyst chemical composition utilized. However, time periods of up to about 50 hours, preferably about 0.3 to about 30 hours, and more preferably about 1 to about 5 hours may be utilized in order to provide desirable catalyst activation.

As previously set forth herein, catalyst activated by processes of the present invention may be utilized in hydroxylation of aromatic compounds. Accordingly, activation utilizing the present invention may precede such hydroxylation process and may be performed in the same reaction vessel. Subsequent to the present activation process, the hydroxylation process may be conducted as described in U.S. Pat. Nos. 5,055,623; 5,001,280; 5,110,995; and 5,756,861, the entire subject matter of which is incorporated herein by reference. Typically the reaction is carried out with a molar deficiency of the nitrous oxide. In addition to vaporized aromatic compound and nitrous oxide, the reactant gas feed to the catalyst can contain a variety of other gases as diluents or contaminants. Diluents typically will not adversely effect the desired reaction to produce the oxidized aromatic product, e.g., phenol, and typically comprise helium, argon, nitrogen, carbon dioxide or other such gases or mixtures thereof. Contaminants are characterized as species that adversely effect the desired reaction to produce the oxidized aromatic product whether by participating in a competing reaction or poisoning of the catalyst. The amount of contaminants is preferably very low, but in view of the practical difficulty of providing pure gases in industrial applications, certain low levels of contaminants can be tolerated. Contaminants typically found in industrial gas streams that can be tolerated at low levels include water vapor, ammonia, oxygen, carbon monoxide, nitric oxide, nitrogen dioxide and volatile organic species.

In addition to benzene, the aromatic compound may be any of a variety of substituted benzenes such as phenol, fluorobenzene, chlorobenzene, toluene, ethylbenzene and similar compounds having an aromatic ring with a substitutable hydrogen atom on the ring. The process can be used to produce polyols, e.g., hydroquinone, resorcinol and catechol, by oxidation of phenol. Thus, when phenol is produced from oxidation of benzene, the phenol product can be further oxidized by contact with the catalyst. Undesirable production of polyols can be avoided by employing a low ratio of nitrous oxide to aromatic compound, e.g., about 0.5 or lower, and by minimizing catalyst residence time. Similarly, a mixture of polyols can be prepared by extending catalyst residence time. Generally, it is preferred to keep catalyst contact time at a low level to preclude production of unwanted polyols. Such residence time can readily be determined by a person skilled in the art by routine experimentation in view of reaction conditions, catalyst activity, feed compositions, catalyst bed size and the like.

By conducting reductive activation according to the present invention, the productivity of any subsequent aromatic hydroxylation is increased substantially (e.g., up to and over 2 times without reductive activation).

In another embodiment of the present invention, a deactivated zeolite catalyst is reactivated by exposing said catalyst to a reducing atmosphere. Such reductive reactivation may be performed on zeolite catalysts utilized in the previously mentioned hydroxylation of aromatics processes. Typically, coke forms on and/or in the zeolite catalyst during the hydroxylation process, which must be removed periodically by burning off the coke. Coke removal is conducted by heating the catalyst at temperatures above 600° C. Such zeolite catalysts may become deactivated by prolonged exposure to high temperatures (e.g., above 600° C.) used in coke removal processes. Additionally, a further decrease in catalyst activity is attributed to high concentrations of water vapor formed during such coke removal. The reactivation of the catalyst is conducted under the same conditions and with the same reductive atmosphere as previously mentioned for catalyst activation according to the present invention. The reactivated catalyst may then be again utilized in hydroxylation processes.

In another embodiment of the present invention, activity loss of a zeolite catalyst that occurs during the production of hydroxylated aromatic compounds may be prevented and/or reduced by reacting the aromatic compounds with nitrous oxide in the presence of the zeolite catalyst and concurrently exposing the catalyst to a reducing atmosphere. Such a process may be conducted by the hydroxylation process mentioned herein with the addition of a reducing atmosphere in the amounts as set forth herein.

EXAMPLES

The benefits and advantages of the process of this invention are illustrated by reference to the following examples in which the reductive activation process is utilized on zeolite catalysts of various reactions of benzene oxidation to phenol in a plug flow reactor. Activation and reactivation of zeolite catalysts are performed according to the present invention. The activation and reactivation conditions and calculated reaction parameters are reported in the Tables 1–6.

Examples 1–3 (Comparative)

In the examples, the Fe-containing zeolite catalyst of ZSM-11 structure is used. The catalyst composition is as follows: $SiO_2/Al_2O_3$=40; $CF_e$=0.08 wt %; $CN_a$ 0.02 wt %; the BET surface area is 320 $m^2$/g; and the micropore volume is 0.136 $cm^3$/g. The zeolite is prepared by hydrothermal synthesis with iron introduction into the initial gel according to the process set forth in U.S. Pat. No. 5,110,995, the entire subject matter of which is incorporated herein by reference. After burning off the organic template and transformation of the zeolite into H-form, the catalyst, for conventional activation purposes, is subjected to additional calcination at one of the temperatures reported in Table 1. To test the catalytic properties of the activated catalyst, 0.5–1.0 mm of catalyst is loaded into a quartz tube reactor with an inner diameter of 7 mm. The reactor is heated up to 400° C., and the reaction mixture (5 mol % $N_2O$, 50 mol % $C_6H_6$, helium the balance) is fed at a rate of 2 $cm^3$/s. The reaction mixture composition at the reactor outlet is analyzed periodically by chromatography. Phenol productivity of the catalyst is calculated from the obtained data. The productivity measured 1 hour after the onset of the reaction is presented in Table 1 (Examples 1–3).

Examples 1–3 typify the prior art and illustrate the efficiency of purely thermal activation conducted according to the method set forth in EP 088 9018 A1. This method was chosen as a prototype, and it will be compared to activation in the presence of a reductant according to the present invention.

The initial zeolite calcined at 550° C. exhibits minor activity (Example 1). Its phenol productivity comprises only 1.5 mmol/g.h. The activity grows with the elevation of the calcination temperature (Examples 2–3).

Examples 4–6

A FeZSM-11 catalyst of the same chemical composition and the same preparation method as in Examples 1–3 is synthesized. After burning off the organic template and transformation of the zeolite into H-form, the catalyst is activated in He flow containing 6 mol % of carbon monoxide (as a reductant) at temperatures listed in Table 2. After activation, the catalyst is tested in the reaction of benzene hydroxylation to phenol using nitrous oxide under the conditions as set forth in Examples 1–3. A comparison of Examples 1–3 (Table 1) with Examples 4–6 (Table 2) demonstrates that the activation under CO presence considerably increases the zeolite activity.

Examples 7–12 (Comparative)

Zeolite catalyst of ZSM-5 structure is prepared according to the process described in U.S. Pat. No. 5,110,995. The catalyst does not contain a specially introduced Fe or any other transition metal and has the following chemical compositions: $SiO_2/Al_2O_3$=80; $CN_a$=0.01 wt %. The catalyst BET surface area is 375 $m^2$/g and the micropore volume is 0.148 $cm^3$/g. After burning off the organic template and transformation into H-form, the catalyst is subjected to steam activation according to U.S. Pat. No. 5,672,777 at one of temperatures listed in Table 3. The activation is carried out for 2 hours in helium flow containing 50 mol % $H_2O$. Comparison with the results of Example 7 performed with non-activated catalyst shows that steam activation considerably increases the zeolite catalytic activity. This method was chosen as a prototype for comparison with reductive steam activation performed in the presence of water vapor and a reducing gas according to the present invention (Examples 13–17).

Examples 13–17

ZSM-5 zeolite of the same chemical composition and the same preparation method as in Examples 7–12 is prepared. After burning off organic template and transformation into H-form, the catalyst is subjected to steam activation in the presence of CO at temperatures listed in Table 4. The composition of activating mixture is 50 mol % $H_2O$, 6 mol % CO, helium the balance. These Examples, compared to Examples 7–12, illustrate the positive effect of a reductant in combination with steam activation. Due to CO pretreatment, phenol productivity increases up to 75% depending on the activation temperature.

Examples 18–21

Examples 18–21 illustrate the effect of the nature of various reductants used in combination with steam activation. In these examples, the samples of ZSM-5 zeolite are prepared in the same manner as done in Example 15, except that ammonia (Example 19), hydrogen (Examples 20 and 21), and methane (Example 22) are used as a reductant in the activation instead of CO.

Results reported in Table 5 illustrate that the reductant presence increases the catalytic activity of the ZSM-5 zeolite in all cases. Phenol productivity grows nearly 2-fold: from 5.1 mmol PhOH/g.h in Example 10 (activation without a reductant) to 9.0–10.5 mmol/g.h in Examples 18–21. Therewith, the concentration and nature of a reductant do not substantially affect the value of activating effect. This demonstrates the ability according to the present invention to select a suitable reductant among various organic and inorganic substances.

Example 22 (Comparative)

A sample of ZSM-5 zeolite is prepared in the same fashion as in Example 11. Then the catalyst is subjected to deactivation by a long-time high temperature treatment in the presence of water vapor. Such treatment simulates the actual conditions that the catalyst would encounter during use in oxidation (with regeneration) processes. As seen from Table 6, the catalyst loses considerable activity. Its productivity falls from 4.3 mmol PhOH/g.h (Example 11) to 1.9 mmol PhOH/g.h.

In this Example, the sample was deactivated with the aim to further test the possibility of its reactivation by reductive treatment according to the present invention (see Example 23).

Example 23

This example illustrates the feasibility of deactivated zeolite reactivation. With this aim, the deactivated ZSM-5 sample of Example 22, which exhibited low catalytic activity, was subjected to reductive treatment at 775° C. in helium flow containing 12 mol % CO. Such treatment increases the catalytic activity of the sample several times and results in a complete restoration of its phenol productivity (Table 6).

TABLE 1

Activation of FeZSM-5 zeolite by its calcination in air

| Example # | Calcination temperature, ° C. | Phenol productivity, mmol PhOH/g · h |
|---|---|---|
| 1 | 550 | 1.5 |
| 2 | 650 | 2.2 |
| 3 | 800 | 6.8 |

TABLE 2

Activation of FeZSM-5 zeolite in CO presence

| Example # | Calcination temperature, ° C. | Phenol productivity, mmol PhOH/g · h |
|---|---|---|
| 4 | 550 | 2.0 |
| 5 | 650 | 4.0 |
| 6 | 800 | 11.0 |

TABLE 3

Steam activation of ZSM-5 zeolite

| Example # | Activation temperature, ° C. | Phenol productivity, mmol PhOH/g · h |
|---|---|---|
| 7 | Without activation | 0.90 |
| 8 | 400 | 2.1 |
| 9 | 500 | 7.5 |
| 10 | 600 | 5.1 |
| 11 | 700 | 4.3 |
| 12 | 800 | 1.1 |

TABLE 4

Steam activation of ZSM-5 zeolite in CO presence (6 mol. %)

| Example # | Activation temperature, ° C. | Phenol productivity, mmol PhOH/g · h |
|---|---|---|
| 13 | 400 | 2.6 |
| 14 | 500 | 8.2 |
| 15 | 600 | 8.5 |
| 16 | 700 | 6.0 |
| 17 | 800 | 1.7 |

TABLE 5

Steam activation of ZSM-5 zeolite in the presence of various reductants

| Example # | Reducer | Reducer concentration, mol % | Phenol productivity, mmol PhOH/g · h |
|---|---|---|---|
| 18 | $NH_3$ | 6.0 | 10.5 |
| 19 | $H_2$ | 3.5 | 9.5 |
| 20 | $H_2$ | 100 | 9.0 |
| 21 | $CH_4$ | 4.7 | 9.0 |

TABLE 6

Reactivation of deactivated ZSM-5 zeolite

| Example # | Reactivation temperature, ° C. | Phenol productivity, mmol PhOH/g · h |
|---|---|---|
| 22 | Without reactivation | 1.9 |
| 23 | 775 | 5.0 |

The preceding description of specific embodiments of the present invention is not intended to be a complete list of every possible embodiment of the invention. Persons skilled in this field will recognize that modifications can be made to the specific embodiments described herein that would be within the scope of the present invention.

What is claimed is:

1. A method for catalytic production of hydroxylated aromatics comprising, exposing zeolite catalyst to a reducing atmosphere to activate said catalyst, and reacting an aromatic with nitrous oxide in the presence of said activated catalyst.

2. A method according to claim 1, wherein said reducing atmosphere comprises a reductant, water or inert gas.

3. A method according to claim 1, wherein said reductant comprises carbon monoxide, hydrogen, ammonia, hydrogen monoxide, methane, ethane, benzene, methanol, ethanol or mixtures thereof.

4. A method according to claim 1, wherein said reductant comprises carbon monoxide.

5. A method according to claim 1, wherein said reducing atmosphere comprises from about 1.0 to about 99.0 vol. % water.

6. A method according to claim 1, wherein said reducing atmosphere comprises from about 2 to about 10 vol. % reductant and from about 30 to about 60 vol. % water.

7. A method according to claim 1, wherein said activating is conducted at a temperature comprising from about 300 to about 1000° C.

8. A method according to claim 1, wherein said activating is conducted for a period of time from about 0.3 to about 30 hours.

9. A method for restoring activity of a deactivated zeolite catalyst utilized in the production of hydroxylated aromatics comprising, exposing said zeolite catalyst to a reducing atmosphere.

10. A method according to claim 9, wherein said reducing atmosphere comprises a reductant, water or inert gas.

11. A method according to claim 9, wherein said reductant comprises carbon monoxide, hydrogen, ammonia, hydrogen monoxide, methane, ethane, benzene, methanol, ethanol or mixtures thereof.

12. A method according to claim 9, wherein said reductant comprises carbon monoxide.

13. A method according to claim 9, wherein said reducing atmosphere comprises from about 1.0 to about 99.0 vol. % water.

14. A method according to claim 9, wherein said reducing atmosphere comprises from about 2 to about 10 vol. % reductant and from about 30 to about 60 vol. % water.

15. A method according to claim 9, wherein said activating is conducted at a temperature comprising from about 300 to about 1000° C.

16. A method according to claim 9, wherein said activating is conducted for a period of time from about 0.3 to about 30 hours.

17. A method for reducing activity loss of a zeolite catalyst during production of hydroxylated aromatics comprising, reacting an aromatic with nitrous oxide in the presence of said zeolite catalyst, and exposing said catalyst during said reacting to a reducing atmosphere.

18. A method according to claim 17, wherein said reducing atmosphere comprises a reductant, water or inert gas.

19. A method according to claim 17, wherein said reductant comprises carbon monoxide, hydrogen, ammonia, hydrogen monoxide, methane, ethane, benzene, methanol, ethanol or mixtures thereof.

20. A method according to claim 17, wherein said reductant comprises carbon monoxide.

21. A method according to claim 17, wherein said reducing atmosphere comprises from about 1.0 to about 99.0 vol. % water.

22. A method according to claim 17, wherein said reducing atmosphere comprises from about 2 to about 10 vol. % reductant and from about 30 to about 60 vol. % water.

23. A method method according to claim 17, wherein said activating is conducted at a temperature comprising from about 300 to about 1000° C.

24. A method according to claim 17, wherein said activating is conducted for a period of time from about 0.3 to about 30 hours.

* * * * *